United States Patent [19]

Toscano

[11] Patent Number: 4,514,562
[45] Date of Patent: Apr. 30, 1985

[54] FLUORINATED ERYTHROMYCIN COMPOUNDS AND A PROCESS FOR PREPARATION

[75] Inventor: Luciano Toscano, Milan, Italy

[73] Assignee: Pierrel Spa, Napoli, Italy

[21] Appl. No.: 443,580

[22] Filed: Nov. 22, 1982

[30] Foreign Application Priority Data

Nov. 27, 1981 [IT] Italy ................. 25345 A/81

[51] Int. Cl.$^3$ ............................................. C07H 17/04
[52] U.S. Cl. ...................................... 536/7.2; 536/7.4; 536/122
[58] Field of Search ........................... 536/7.2, 7.4, 122

[56] References Cited

U.S. PATENT DOCUMENTS 2,812,323  11/1957  Flynn et al. .......................... 536/7.2
3,674,773  7/1972  Kurath ................................ 536/7.2

FOREIGN PATENT DOCUMENTS 0056291  7/1982  European Pat. Off. ............. 536/7.2

OTHER PUBLICATIONS

Haynes et al., "Advances In Carbohydrate Chem.", vol. 10, pp. 207–213, 1955.
Hough et al., "Jour. Chem. Soc.", #20, pp. 2513–2517, 1972.

*Primary Examiner*—Johnnie R. Brown
*Attorney, Agent, or Firm*—Murray, Whisenhunt and Ferguson

[57] ABSTRACT

Fluorinated derivatives of erythromycins A, B, C and D, having antibiotic activity, are prepared, starting from 8,9-anhydroerythromycin 6,9-hemiacetals or their N-oxides, through the reaction with a compound capable of generating electrophilic reactive fluorine, the resulting reaction product undergoing thereafter a reduction, possibly together with a methylation, to the corresponding (8S)-8-fluoroerythomycins.

24 Claims, No Drawings

FLUORINATED ERYTHROMYCIN COMPOUNDS AND A PROCESS FOR PREPARATION

The present invention relates to the preparation of the macrolide antibiotics, namely (8S)-8-fluoroerythromycin A (P-80206), (8S)-8-fluoroerythromycin B (P-80203), (8S)-8-fluoroerythromycin C (P-80205) and (8S)-8-fluoroerythromycin D (P-80202), useful as antibacterial agents and having the general formula:

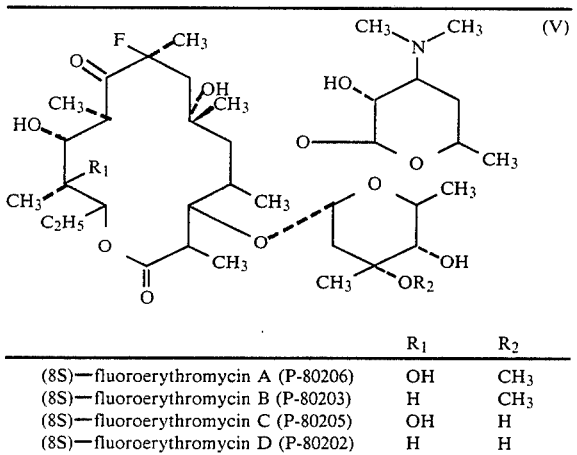

| | $R_1$ | $R_2$ |
|---|---|---|
| (8S)—fluoroerythromycin A (P-80206) | OH | $CH_3$ |
| (8S)—fluoroerythromycin B (P-80203) | H | $CH_3$ |
| (8S)—fluoroerythromycin C (P-80205) | OH | H |
| (8S)—fluoroerythromycin D (P-80202) | H | H |

(wherein the bracketed abbreviations correspond to the internal reference numbers of the Applicant).

The invention relates as well to novel intermediates and to the related synthesis process.

The macrolide antibiotics of the present invention are useful as antibacterial agents and have been described in the European Patent Application No. 82.200019.6 of the same Applicant.

The (8S)-8-fluoroerythromycin A does exist in different crystalline forms, comprising at least two anhydrous forms (nedle like and prysmatic), a solvated anhydrous form (ethanol,prysmatic) and two hydrated forms A and B, the latter being a lamellar form, which can be revealed with respect to one another by means of crystallographic analysis methods (such as X rays, powder method), by Kofler melting point and by differential thermal analysis (DSC). These crystalline forms have different chemical and physical properties as well as different biological properties. In the afore said patent application there are also disclosed microbiological methods for their preparation, based on the use both of blocked mutants of the species S. erythreus and of substrates formed by derivatives of erythronolide A and erythronolide B.

As is well known an alternative route, which is often preferred for the preparation of antibiotics is that of the partial or total chemical synthesis, since it often has not negligible advantages from the point of view of the industrial production and of the control, isolation and purification of the desired products.

The main object of the present invention is that of providing a process for the partially synthetic preparation of (8S)-8-fluorinated macrolidic antibiotics of the class of erythromycins.

This object is achieved by a process for the preparation of (8S)-8-fluoroerythromycin having the formula

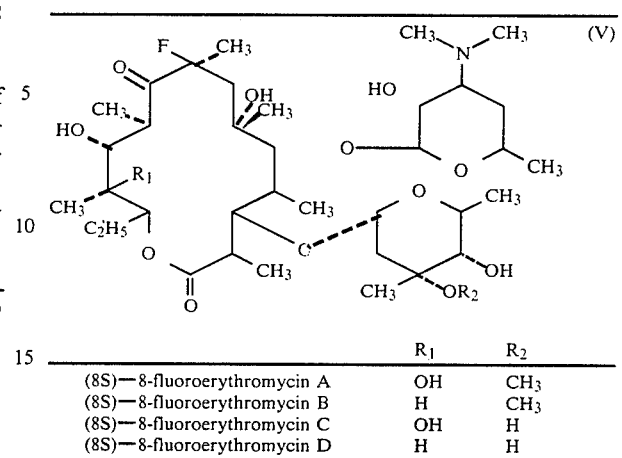

| | $R_1$ | $R_2$ |
|---|---|---|
| (8S)—8-fluoroerythromycin A | OH | $CH_3$ |
| (8S)—8-fluoroerythromycin B | H | $CH_3$ |
| (8S)—8-fluoroerythromycin C | OH | H |
| (8S)—8-fluoroerythromycin D | H | H | characterized by the steps of:

(a) reacting a compound having the formula (I) or (III)

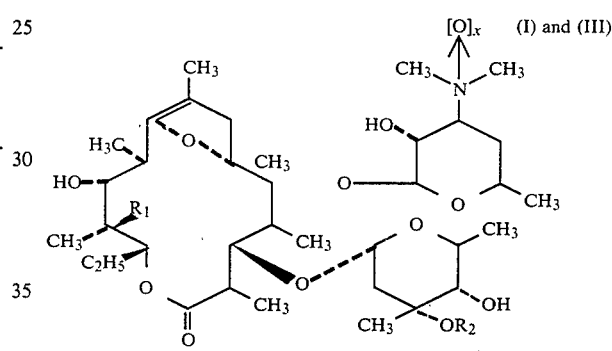

wherein $R_1$ and $R_2$ have the above mentioned meanings and x represent 0 or 1, with a compound capable of generating electrophilic fluorine, to form the compounds having general formula (II) or (IV)

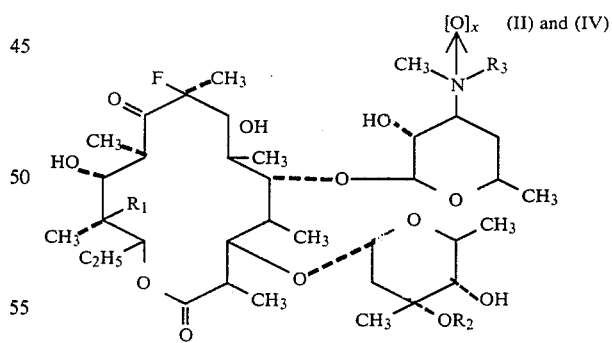

wherein $R_1$, $R_2$ and x have the above indicated meanings and $R_3$ is $CH_3$ when x=1, whereas $R_3$ is H when x=0, and (b) reduction of the compound (II) or (IV), possibly together with a methylation if x=0 and $R_3$=H, to form the compounds (V).

The chemical process for the preparation of the novel intermediates and of the novel (8S)-8-fluoroerythromycins A, B, C and D according to the present invention is represented in the following scheme I according to the two methods a and b corresponding to the two meanings of x, whereby the formulas I and II correspond to the formulas III and IV with or without the protective group at the nitrogen atom, respectively, and $R_3$ can be either hydrogen or methyl.

Among the reactants of the fluoroxy-perfluoroalkane class, those mostly used are the fluoroxy-trifluoromethane, which is commercially available, and the fluoroxy-pentafluoroethane, which can be readily

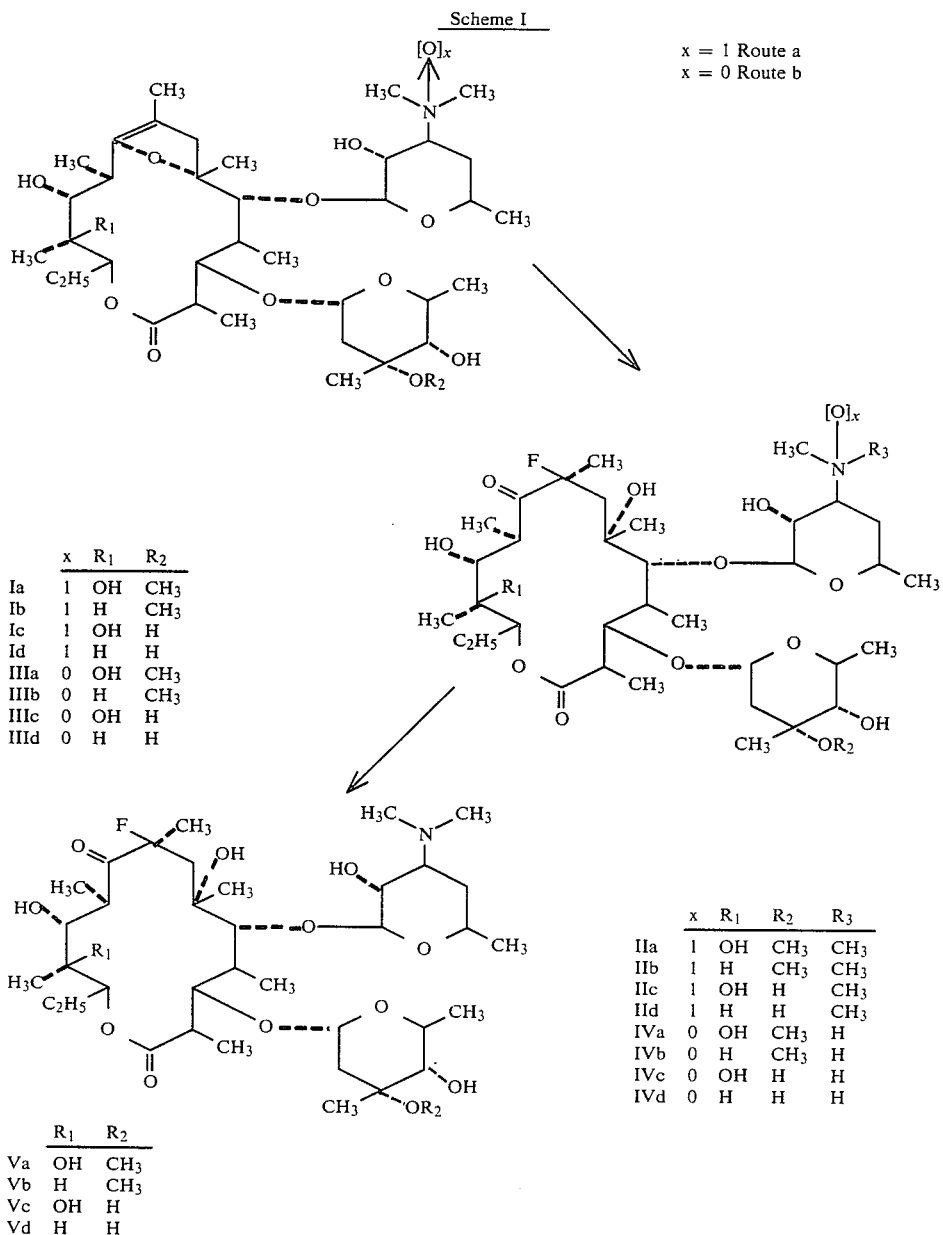

Scheme I

Whereas the 8,9-anhydroerythromycins A and B 6,9-hemiacetals and the 8,9-anhydroerythromycins A and B 6,9-hemiacetal N-oxides are known, the corresponding derivative C and D are not described in the literature and have been obtained from erythromycins C and D, by using known methods.

Referring to the first part of both synthesis routes, the most used reactants capable of generating electrophilic fluorine comprise perchlorylfluoride, fluoroxy-perfluoroalkanes (having general formula $C_nF_{2n+1}OF$), molecular fluorine, trifluoroacetylhypofluorite (as prepared according to J. Org. Chem. 45, 672 (1980)), fluoroxysulfurpentafluoride and lead tetracetate-hydrogen fluoride.

prepared according to J. Org. Chem. 45, 4122, (1980). The molecular fluorine can be used either diluted with an inert gas (for example, argon, nitrogen), or as $F_2$-pyridine, (this compound being obtainable according to Z. Chem. 12, 292 (1972)), or even in form diluted with acetic acid (Collection Czechoslav. Chem. Commun. 42, 2694 (1977)).

As the reaction solvents, there are included the chlorinated hydrocarbons, such as trichlorofluoromethane (Freon 11), chloroform, methylene chloride and the like, tetrahydrofuran or dioxane, possibly diluted with water, pyridine and their mixtures. In the fluorination with fluoroxy-perfluoroalkanes and molecular fluorine the reaction is preferably carried out at low temperatures, most preferably between −75° C. and −85° C., under continuous stirring. When perchloryl fluoride is used, it is preferred to carry out the reaction in the range of −10° C. to +10° C. The reaction is normally completed in a time of between about 15 minutes and one hour, and is preferably carried out in the presence of an organic base, such as pyridine, quinoline, triethylamine, or of an inorganic base, such as calcium oxide, sodium or potassium acetate.

As regards the second step of both synthesis routes, the hydrogenation is carried out in ethanol in the presence of a catalyst consisting of palladium supported on carbon, by operating at room temperature and at one atmosphere of hydrogen pressure. Other reaction solvents comprise methanol, ethyl acetate, tetrahydrofuran, dioxane and like solvents.

In the preparation of the compounds of the present invention according to the route a (I→II→V), the N-oxides of 8,9-anhydroerithromycins 6,9-hemiacetals are reacted with a compound capable of generating electrophilic fluorine, preferably selected among fluoroxy-trifluoromethane and perchloryl fluoride, to form the N-oxides of the (8S)-8-fluoroerythromycins, in an inert organic solvent and at low temperature, in the presence of a base as previously identified. The N-oxides are thereafter reduced to give the corresponding products having antibacterial activity.

In the preparation of the compounds of the present invention according to the route b (III→IV→V), the 8,9-anhydroerytrhomycins 6,9-hemiacetals are reacted with a compound capable of generating electrophilic fluorine, like the above indicated ones and under the same conditions, without protection of the N-dimethyl group present in the 3 position of the desosamine sugar.

When this reaction is completed, the N-monomethylated, (8S)-8-fluoroerythromycins which are present in the reaction mixture, are converted to the corresponding (8S)-8-fluoroerythromycins by reductive methylation with formaldehyde and hydrogen.

As regards the novel intermediates of the present invention, the following compounds are contemplated:
(1) (8S)-8-fluoroerythromycin N-oxides having the formula:

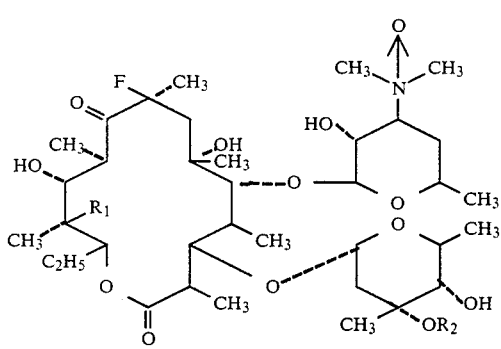

wherein $R_1$ and $R_2$ have the above stated meanings.
(2) de(N-methyl)-(8S)-8-fluoroerythromycins having the formula

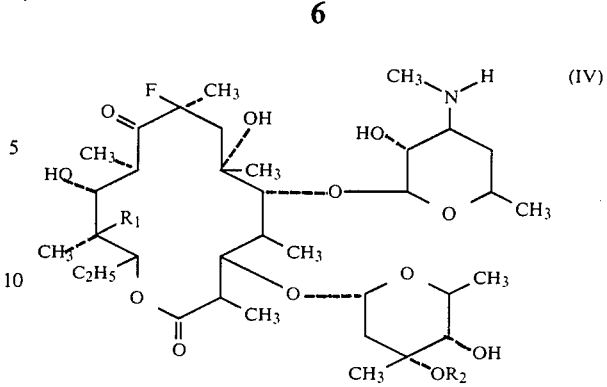

wherein $R_1$ and $R_2$ have the above stated meanings.

The following non-limitative examples illustrate the scope of this invention.

EXAMPLE 1

Preparation of (8S)-8-fluoroerythromycin A N-oxide (IIa) by fluorination of 8,9-anhydroerythromycin A 6,9-hemiacetal N-oxide (Ia)

(a) by fluoroxy-trifluoromethane.

A solution of fluoroxy-trifluoromethane ($CF_3OF$) in $CCl_3F$ was prepared at −80° C. as follows a $CF_3OF$ excess (about 2 equivalents) was dissolved in $CCl_3F$ (previously cooled to 80° C.), by slowly adding the gas through a sparger, while the $CF_3OF$ containing cylinder was continuously weighed. The concentration thereof was determined by iodometric titration.

The solution of $CF_3OF$ in $CCl_3F$ at about −80° C. was slowly added under electromagnetic stirring to a mixture comprising 7.320 g (0.010 moles) of 8,9-anhydroerythromycin A 6,9-hemiacetal N-oxide (Ia), (described in the U.S. Pat. No. 3,674,773) and 3.84 g of calcium oxide in $CCl_3F/CH_2Cl_2$ (295 mls/370 mls) cooled at about −80° C. The reaction course was periodically monitored by high pressure liquid chromatography (HPLC), by checking the disappearance of the compound Ia.

When the peak of the compound Ia had disappeared or was reduced to a minimum, the stirring was continuated for 5 minutes and nitrogen gas was bubbled in the reaction mixture maintained at −80° C. to remove the $CF_3OF$ excess. The temperature of the mixture spontaneously rose to room temperature and the mixture was filtered; the organic solution was washed with a saturated solution of $NaHCO_3$ (650 mls), with water until neutral, dried over $Na_2SO_4$ and evaporated under vacuum at 50° C., yielding a residue (7.300 g). The crude product contained at least three reaction products, one of which was identified as (8S)-8-fluoroerythromycin A N-oxide (IIa) by HPLC comparison with a standard sample as prepared by oxidizing with hydrogen peroxide (8S)-8-fluoroerythromycin A, which in turn had been prepared by fermentation with Streptomyces erythreus ATCC 31772, using (8S)-8-fluoroerythronolide A as the substrate (according to the already mentioned European Patent Application).

To this end, 0.752 g (0.001 mol) of the said (8S)-8-fluoroerythromycin A (Va) were dissolved in 45 mls of 60% methanol containing 3% of hydrogen peroxide. The resulting solution was maintained at rest for 48 hours, then the methanol was distilled under vacuum. The aqueous suspension was extracted with chloroform (50 mls×3).

After drying over anhydrous Na₂SO₄, the chloroformic solution was evaporated to dryness. By crystallization from methanol/ethyl ether, 0.735 g of (8S)-8-fluoroerythromycin A N-oxide (IIa) were obtained, having the following properties:

m.p.: 168°–169° C.

$[\alpha]_D^{20}$: −63.3° (C=1 in methanol).

U.V. (methanol): 286 nm ($\epsilon$12.2).

I.R. (KBr): 3480 (wide), 1730, 1640, 1460, 1380, 1345, 1190 (shoulder), 1170, 1125, 1110, 1080, 1060, 1030, 1015, 1000, 980, 960, 935, 900, 875, 835, 805 cm⁻¹.

The analysis for $C_{37}H_{66}FNO_{14}$ gave the following values: Calculated (percent): C 57.87; H 8.66; F 2.47; N 1.82. Found (percent): C 57.95; H 8.62; F 2.43; N 1.87.

(b) by perchloryl fluoride.

Perchloryl fluoride (18 to 20 g) was slowly bubbled through a sparger in a solution containing 10 g (0.0137 mol) of 8,9-anhydroerythromycin A 6,9-hemiacetal N-oxide (Ia), described in U.S. Pat. No. 3,674,773, in tetrahydrofuran (150 mls), pyridine (50 mls) and water (50 mls) at ±5° C.

The reaction course was periodically monitored by HPLC, looking for the disappearance of the characteristic peak of the starting compound.

After disappearance (or minimizing) of the peak corresponding to the compound Ia, nitrogen was bubbled through the reaction solution, which was slowly raised to room temperature. The solution was concentrated under vacuum at 50° C. to 100 mls, 50 mls of water were added and the resulting mixture was extracted with methylene chloride (150 mls×4).

The organic solution was dried over Na₂SO₄ and evaporated until a final solution of compound IIa in pyridine was obtained. This solution was poured under strong mechanical stirring into 1 lt of n-hexane, previously cooled to 0° C. After one night standing at this temperature the flocky precipitate was filtered, washed with 20 mls of ethyl ether and dried.

The solid product (10.5 g), was identified as (8S)-8-fluoroerythromycin A N-oxide (IIa), by HPLC comparison with a standard sample. The raw solid product was used as such in the next hydrogenolysis reaction.

EXAMPLE 2

Preparation of (8S)-8-fluoroerythromycin A (Va) by reduction of (8S)-8-fluoroerythromycin A N-oxide (IIa)

(a) The solution of 7.300 g of crude product as obtained in the example 1a, containing the (8S)-8-fluoroerythromycin A N-oxide (IIa), in 600 mls of absolute ethanol was hydrogenated (1 atm of H₂ pressure, 28° C.) in the presence of 2.920 g of 5% Pd/C for 2 hours. The catalyst was thereafter filtered and washed several times with ethanol. The combined filtrates were evaporated to give 7.100 g of residue which, after repeated crystallizations from absolute ethanol, gave 0.865 g of (8S)-8-fluoroerythromycin A (Va) having the following properties:

m.p.: 184°–5° C.

$[\alpha]_D^{20}$ −57.6° (C=1 in methanol).

U.V. (methanol: 285 nm ($\epsilon$9.9).

I.R. (KBr): 3520, 3480, 3280, (shoulder), 1735, 1720, 1460, 1425, 1400, 1370, 1345, 1330, 1305, 1280, 1190, 1170, 1120, 1090, 1075, 1055, 1030, 1015, 1005, 980, 960 (shoulder), 935, 890, 870, 855, 835, 800.

The analysis for $C_{37}H_{66}FNO_{13}$ gave the following results: Calculated (percent): C 59.10; H 8.85; F 2.52; N 1.86. Found (percent): C 59.25; H 8.79; F 2.52; N 1.89.

In a few samples obtained from different runs and maintained under vacuum at 50° C. for 8 hours, the presence of 3 to 6% of ethanol was detected by GLC (gas chromatographic analysis). The (8S)-8-fluoroerythromycin A crystallized from absolute ethanol as a crystalline solvated form. The phase transitions of the solvate from ethanol, which is in prysmatic crystalline form, have been monitored by thermal microscopy using a Kofler instrument. By a heating rate of 2° C./min, the desolvatation is observed at 165°–175° C., followed by melting at 182°–184° C., without any intermediate transition to the amorphous state.

At the thermal analysis (DSC), as carried out with a heating rate of 5° C./min, the compound shows a desolvatation endotherm at 167° C. and a melting endotherm at 183° C.

The raw product can also be purified by partition chromatography in a silica gel column, according to the method described by N. L. Oleinick in J. Biol. Chem., Vol. 244, n. 3, page 727 (1969). The fractions containing (8S)-8-fluoroerytrhomycin A (Va) only were combined, evaporated under vacuum to dryness and crystallized from absolute ethanol to give 1.760 g of (8S)-8-fluoroerythromycin A (Va) having the above indicated properties.

The final yield of (8S)-8-fluoroerythromycin A (Va) was remarkably increased when the hydrogenation residue was dissolved in 235 mls of 50% aqueous acetic acid. After 3 hours at room temperature the solution was made alkaline with NaHCO₃, extracted with methylene chloride and washed with water until neutral.

The organic solution, dried over anhydrous Na₂SO₄, was then concentrated under vacuum at 50° C., giving a crude product (6.95 g) which, by crystallization from absolute ethanol, gave 3.65 g of (8S)-8-fluoroerythromycin A, having the same properties as above indicated.

(b) A solution of 10.5 g of crude (8S)-8-fluoroerythromycin A N-oxide (IIa), as prepared according to the example 1(b), in 865 mls of absolute ethanol was hydrogenated as above indicated. By concentration of the final ethanol solution to 40 ml volume, after cooling overnight to 0° C., 7 g of (8S)-8-fluoroerythromycin A (Va) were obtained, having the afore said chemical and physical properties.

EXAMPLE 3

Preparation of de-(N-methyl)-(8S)-8-fluoroerythromycin A (IVa) by fluorination of 8,9-anhydroerythromycin A 6,9-hemiacetal (IIIa)

(A) By means of fluoroxytrifluoromethane.

A solution of CF₃OF (about 0.02 mol) in CCl₃F, cooled to about −80° C., was slowly added under stirring to a mixture of 7.160 g (0.010 mol) of 8,9-anhydroerythromycin A 6,9-hemiacetal, described by P. Kurath in Experimentia 27, 362 (1971), and of 3.82 g of calcium oxide in CCl₃F/CH₂Cl₂ (295 ml/370 ml) at about −80° C.

After disappearance (or minimizing) of the peak of the compound IIIa, monitored by HPLC, the stirring was continued for 5 minutes; nitrogen gas was then bubbled through the reaction mixture at −80° C. to remove the CF₃OF excess. The temperature of the reaction mixture spontaneously rose to room temperature, then filtered and washed with a saturated solution of NaHCO₃ (650 ml), with water until neutral, dried over Na$_2$SO$_4$ and evaporated under vacuum at 50° C. to give a residue of 7.125 g. The crude product contained at least three reaction products, one of which was identified as de-(N-methyl)-(8S)-8-fluoroerytrhomycin A (IVa) by HPLC comparison with an authentic sample, prepared by N-monodemethylation of (8S)-8-fluoroerythromycin A, obtained by fermentation with *Streptomyces erythreus* ATCC 31772 using (8S)-8-fluoroerythronolide A as the substrate (see above stated European patent Application).

The demethylation was carried out as follows:

A solution of 3.760 g (0.005 mol) of (8S)-8-fluoroerythromycin A (Va), prepared by fermentation, in 37.5 ml of 80% methanol was treated with 0.650 g (0.025 mol) of sodium acetate trihydrate.

The solution was heated to 72° C. and then 1.270 g (0.005 mol) of I$_2$ were added under magnetic stirring.

The pH of the reaction mixture was adjusted to 8.5 with a 1N solution of sodium hydroxide. The mixture was maintained under stirring at 47° C. and at pH 8.5 for 4 hours, cooled at 25° C., decolored with a few milliliters of 5% Na$_2$S$_2$O$_3$, poured in 250 mls of 0.5N NH$_4$OH and then extracted three times with chloroform (250 ml × 3). The chloroformic phase was washed with 1N NH$_4$OH, dried over anhydrous Na$_2$SO$_4$ and evaporated to dryness under vacuum, giving 3.675 g of the compound IVa, not in crystalline form.

EXAMPLE 4

Preparation of (8S)-8-fluoroerythromycin A (Va) by reductive methylation of de-(N-methyl)-(8S)-8-fluoroerythromycin A (IVa)

A solution of 7.125 g of the raw product obtained in example 3, containing the de-N-methyl)-(8S)-8-fluoroerythromycin A (IVa), in 575 ml of absolute ethanol, was supplemented with 30 mls of a 1% formaldehyde solution and hydrogenated (1 atm of H$_2$ pressure, 28° C.) was carried out in the presence of 2.85 g of 5% Pd/C for 48 hours. Upon completion of the hydrogenation, the catalyst was filtered and washed with ethanol several times. The combined filtrates were evaporated to yield 7.185 g of residue and then purified by partition chromatography in a silica gel column according to the method referred to in example 2.

The fractions containing the desired product were combined, evaporated under vacuum to dryness and crystallized from absolute ethanol to give 1.525 g of (8S)-8-fluoroerythromycin A having the same chemical and physical characteristics as reported in example 2.

EXAMPLE 5

Preparation of (8S)-8-fluoroerythromycin B N-oxide (IIb) by fluorination of 8,9-anhydroerythromycin B 6,9-hemiacetal N-oxide (Ib)

(a) by fluoroxy-trifluoromethane

By the general method of example 1(a) the 8,9-anhydroerythromycin B 6,9-hemiacetal N-oxide (Ib), described in U.S. Pat. No. 3,674,773, was converted into a mixture containing several reaction products, one of which was identified as (8S)-8-fluoroerytrhomycin B N-oxide (IIb) by means of HPLC comparison with an authentic sample which was prepared by oxidizing (8S)-8-fluoroerythromycin B (Ib), obtained through fermentation with *Streptomyces erythreus* ATCC 31772 by employing (8S)-8-fluoroerythronolide B as a substrate (European patent Application No. 82.200019.6.)

The oxidation was carried out with hydrogen peroxide according to the method described in example 1 for (8S)-8-fluoroerythromycin A.

Chemical and physical properties of (8S)-8-fluoroerythromycin B N-oxide:

m.p.: 166°–168° C.

$[\alpha]_D^{20} -67.7°$ (C=1 in methanol).

UV (methanol): 287 nm ($\epsilon$23.3).

IR (KBr): 3470 (broad) 1725, 1635, 1460, 1375, 1335, 1185, 1165, 1125, 1110, 1075, 1060, 1010 (shoulder), 1000, 980, 965 (shoulder), 940, 910, 890, 850, 830, 805 cm$^{-1}$.

The analysis for C$_{37}$H$_{66}$FNO$_{13}$ gave the following values: Calculated (percent): C 59.10; H 8.85; F 2.52; N 1.86. Found (percent): C 59.02; H 8.72; F 2.57; N 1.91.

(b) by perchloryl fluoride.

By the general method of example 1(a), 10 g of 8,9-anhydroerythromycin B 6,9-hemiacetal N-oxide, described in U.S. Pat. No. 3,674,773, were converted into (8S)-8-fluoroerytrhomycin B N-oxide (IIb) using perchloryl fluoride as fluorinating agent. The solid product (10.2 g) was identified by HPLC in comparison with an authentic sample prepared from (8S)-8-fluoroerythromycin B, the latter being in turn prepared by fermentation with *Streptomyces Erythreus* ATCC 31772, using (8S)-8-fluoroerythronolide B as the substrate, then subjected to oxidation with hydrogen peroxide as reported in example 1.

EXAMPLE 6

Preparation of (8S)-8-fluoroerythromycin B (Vb) by reduction of (8S)-8-fluoroerythromycin B N-oxide (IIb)

(a) with reference to the method described in example 2, the raw product obtained in example 5(a) was hydrogenated in presence of 5% Pd/C. A solid residue was obtained which, after being reacted with 50% acetic acid and then purified by partition chromatography in a silica gel column according to the method of example 2, yielded (8S)-8-fluoroerythromycin B (Vb) having the following characteristics:

m.p.: 162°–164° C.

$[\alpha]_D^{20} -71.2°$ (C=1 in methanol).

UV (methanol): 287 nm ($\epsilon$25.2).

IR (KBR): 3480 (broad), 1735, 1465, 1435, 1385, 1375, 1330, 1305, 1280, 1170, 1115, 1090, 1075, 1055, 1035, 1020, 1000, 975, 940, 890, 835, 805 cm$^{-1}$.

The analysis for C$_{37}$H$_{66}$FNO$_{12}$ gave the following values: Calculated (percent) C 60.39; H 9.04; F 2.58; N 1.90. Found (percent) C 60.35; H 9.07; F 2.62; N 1.87.

(b) After hydrogenation, according to example 2, of the raw product obtained in example 5(b) which corresponds to the (8S)-8-fluoroerythromycin B N-oxide only, the concentration of the final ethanol solution yielded 6,9 g of (8S)-8-fluoroerythromycin B (Vb) having the same characteristics as above.

EXAMPLE 7

Preparation of de-(N-methyl)-(8S)-8-fluoroerythromycin B (IVb) by fluorination of 8,9-anhydroerythromycin B 6,9-hemiacetal (IIIb)

By the method reported in example 3, (a), the 8,9-anhydroerythromycin B 6,9-hemiacetal, described by P. Kurat in Experimentia 27, 362 (1971), was converted into a raw product wherein de-(N-methyl)-(8S)-8-fluoroerythromycin B (IVb) was identified by HPLC comparison with an authentic sample as prepared by mono-N-demethylation of (8S)-8-fluoroerythromycin B, in turn prepared by fermentation with *Streptomyces erythreus* ATCC 31772 using (8S)-8-fluoroerytrhonolide B as the substrate (European patent application No. 82200019.6).

The monodemethylation was carried out with $I_2$ in presence of sodium acetate according to the method described in example 3.

EXAMPLE 8

Preparation of (8S)-8-fluoroerythromycin B (Vb) by reductive methylation of de-(N-methyl)-(8S)-8-fluoroerytrhomycin B (IVb)

By the general method of example 4, the crude product as obtained in the example 7, dissolved in ethanol and supplemented with 1% formaldehyde, was hydrogenated in the presence of 5% Pd/C. The solid residue was then purified by partition chromatography in a silica gel column as in example 2, to give (8S)-8-fluoroerythromycin B (Vb) having the same chemical and physical characteristics as reported in example 6.

EXAMPLE 9

Preparation of 8,9-anhydroerythromycin C 6,9-hemiacetal N-oxide (Ic) from erythromycin C 8,9-anhydroerythromycin C 6,9-hemiacetal N-oxide (Ic) was prepared from erythromycin C, isolated from the fermentation broths of erythromycin A, according to the method reported in U.S. Pat. No. 3,671,773 for the 8,9-anhydroerythromycin A 6,9-hemiacetal N-oxide (Ia).

EXAMPLE 10

Preparation of (8S)-8-fluoroerythromycin C N-oxide (IIc) by fluorination of 8,9-anhydroerythromycin C 6,9-hemiacetal N-oxide (Ic)

(A) by fluoroxy-trifluoromethane.

By the general method of example 1(a), the 8,9-anhydroerythromycin C 6,9-hemiacetal N-oxide (Ic) was converted into a mixture of products among which (8S)-8-fluoroerythromycin C N-oxide (IIc) was identified by HPLC comparison with an authentic sample prepared by oxidation of (8S)-8-fluoroerythromycin C, as obtained by fermentation carried out with *Streptomyces erythreus* ATCC 31772 using (8S)-8-fluoroerythronolide A as substrate (European patent application No. 8200019.6).

The oxidation was carried out with hydrogen peroxide according to the method described in example 1(a).

(b) by perchloryl fluoride.

By the general method of example 1b, 8,9-anhydroerythromycin C 6,9-hemiacetal N-oxide (Ic) (2 g) was converted to (8S)-8-fluoroerythromycin C N-oxide (IIc) by means of perchloryl fluoride as the fluorinating agent. The crude solid (1.95 g) was identified by HPLC comparison with a standard sample prepared from (8S)-8-fluoroerythromycin C, as prepared by fermentation with *Streptomyces erythreus* ATCC 31772 with (8S)-8-fluoroerythronolide A as substrate, and oxidized with hydrogen peroxide, as reported in example 1.

EXAMPLE 11

Preparation of (8S)-8-fluoroerythromycin C (Vc) by reduction of (8S)-8-fluoroerythromycin C N-oxide (IIc).

(a) By referring to the method reported in example 2, the crude product as prepared in example 10a was hydrogenated in the presence of 5% Pd/C.

A solid residue was thus obtained which, after treatment with 50% acetic acid and subsequent purification by partition chromatography in a silica gel column as indicated in example 2, yielded (8S)-8-fluoroerythromycin C (Vc) having the following characteristics:

m.p.: 217°–218° C.

$[\alpha]_D^{20} - 45°$ (C=1 in methanol).

UV (methanol): 284 nm ($\epsilon$22,5).

IR (KBr): 3350, 3500, 3440 (shoulder), 3300 (wide), 1730, 1455, 1425, 1410, 1380, 1360, 1340, 1330, 1305, 1280, 1270, 1245, 1200 (shoulder), 1170 (wide), 1115, 1090, 1075, 1060, 1030, 1010, 1000, 980 (shoulder), 965, 955, 945, 935, 920, 905, 895, 870, 840, 830, 810.

The analysis for $C_{36}H_{64}FNO_{13}$ gave the following results: Calculated (percent) C 58.60; H 8.74; F 2.57; N 1.90. Found (percent) C 58.75; H 8.81; F 2.52; N 1.91.

(b) When the crude product as prepared in example 10(b), which only contains (8S)-8-fluoroerythromycin C N-oxide (IIc), was hydrogenated as described in example 2, by concentration of the final ethanol solution 1.4 g of (8S)-8-fluoroerythromycin C (Vc) were obtained, having the same chemical and physical characteristics as stated above.

EXAMPLE 12

Preparation of 8,9-anhydroerythromycin C 6,9-hemiacetal (IIIc) from erythromycin C 8,9-anhydroerythromycin C 6,9-hemiacetal (IIIc) was prepared from erythromycin C, as isolated from the fermentation broths of erythromycin A, by the same method as described by P. Kurath in Experimentia 27, 362 (1971) for 8,9-anhydroerythromycin A 6,9-hemiacetal (IIIa).

EXAMPLE 13

Preparation of de-(N-methyl)-(8S)-8-fluoroerythromycin C (IVc) by fluorination of 8,9-anhydroerythromycin C 6,9-hemiacetal (IIIc)

With the method reported in example 3(a) the 8,9-anhydroerythromycin C 6,9-hemiacetal was converted to a crude reaction product wherein N-methyl-(8S)-8-fluoroerythromycin C (IVc) was identified by HPLC comparison with a standard as prepared by N-monodemethylation of (8S)-8-fluoroerythromycin C, obtained by fermentation with *Streptomyces erythreus* ATCC 31772 by (8S)-8-fluoroerythronolide A as a substrate (European Patent application No. 82200019.6). The N-mono-demethylation was carried out with $I_2$ in the presence of sodium acetate according to the method as described in example 3.

EXAMPLE 14

Preparation of (8S)-8-fluoroerythromycin C (Vc) by reductive methylation of de-(N-methyl)-(8S)-8-fluoroerythromycin C (IVc)

By the general method of example 4, the crude product as prepared in example 13 was hydrogenated in the presence of 5% Pd/C and of 1% formaldehyde. The thus obtained solid residue was then purified by partition chromatography in a silica gel column carried out according to the method reported in example 2, to give (8S)-8-fluoroerythromycin C having the same chemical and physical characteristics as those indicated in example 11.

EXAMPLE 15

Preparation of 8,9-anhydroerythromycin D 6,9-hemiacetal N-oxide (Id) from erythromycin D The 8,9-anhydroerythromycin D 6,9-hemiacetal N-oxide (Id) was prepared from erythromycin D, as isolated from the fermentation broths of erythromycin A, by the method reported in U.S. Pat. No. 3,674,773 for 8,9-anhydroerythromycin B 6,9-hemiacetal N-oxide (Ib).

EXAMPLE 16

Preparation of (8S)-8-fluoroerythromycin D N-oxide (IId) by fluorination of 8,9-anhydroerythromycin D 6,9-hemiacetal N-oxide (Id)

(a) by means of fluoroxytrifluoromethane.

According to the general method of example 1(a) the 8,9-anhydroerythromycin D 6,9-hemiacetal N-oxide (Id) was converted into a mixture of three reaction products, one of which was identified as (8S)-8-fluoroerythromycin D N-oxide (IId) by HPLC comparison with a standard sample as prepared by oxidation of (8S)-8-fluoroerythromycin D, which in turn was obtained by fermentation with *Streptomyces erythreus* ATCC 31772 using (8S)-8-fluoroerythronolide B as a substrate (European Patent application No. 82.200019.6). The oxidation was carried out by hydrogen peroxide according to the general method of example 2.

(b) by means of perchloryl fluoride.

According to the general method of example 1(b), 2 g of 8,9-anhydroerythromycin D 6,9-hemiacetal N-oxide (Id) were converted to (8S)-8-fluoroerythromycin D N-oxide (IId) by means of perchloryl fluoride as fluorinating agent. The solid raw product (1,9 g) was identified by HPLC comparison with a standard sample as prepared from (8S)-8-fluoroerythromycin D, obtained by fermentation with *Streptomyces Erythreus* ATCC 31772 using (8S)-8-fluoroerythrobolide as the substrate, and oxidated with hydrogen peroxide, as reported in example 2.

EXAMPLE 17

Preparation of (8S)-8-fluoroerythromycin D (Vd) by reduction of (8S)-8-fluoroerythromycin D N-oxide (IId)

(a) With reference to the method reported in example 2, the crude product as prepared in example 16(a) was hydrogenated in presence of 5% Pd/C. A solid residue was obtained which, after reaction with 50% acetic acid and subsequent purification by partition chromatography in a silica gel column according to the method reported in example 3, gave (8S)-8-fluoroerythromycin D (Vd) having the following characteristics:
m.p.: 214°–216° C.
$[\alpha]_D^{20} -64°$ (C=1 in methanol).
UV (methanol): 286 nm ($\epsilon$32).
IR (KBr): 3600, 3520, 3300 (broad), 1730, 1460, 1420, 1385, 1370, 1355, 1345, 1330, 1310, 1275, 1190, 1160, 1100, 1060, 1040, 1030, 1010, 1000, 995, 975, 960, 935, 920, 910, 890, 875, 840, 825, 810 cm$^{-1}$.

The analysis for $C_{36}H_{64}FNO_{12}$ gave the following results: Calculated (percent): C 59.85; H 8.94; F 2.63; N 1.94. Found (percent): C 59.95; H 8.90; F 2.68; N 1.97.

(b) When the crude product obtained in example 16(b), which contains only (8S)-8-fluoroerythromycin D N-oxide (IId), was hydrogenated as in example 2, by concentrating the final ethanolic solution, 1.35 g of (8S)-8-fluoroerythromycin D (IIId) were obtained having the same chemical and physical characteristics as those reported above.

EXAMPLE 18

Preparation of 8,9-anhydroerythromycin D 6,9-hemiacetal (IIId) from erythromycin D 8,9-anhydroerythromycin D 6,9-hemiacetal (IIId) was prepared from erythromycin D, isolated from fermentation broths of erythromycin A, by using the method described by P. Kurath, Experimentia 27, 362 (1971, for the 8,9-anhydroerythromycin B 6,9-hemiacetal (IIIb).

EXAMPLE 19

Preparation of de-(N-methyl)-(8S)-8-fluoroerythromycin D (IVd) by fluorination of 8,9-anhydroerythromycin D 6,9-hemiacetal (IIId)

By following the process of example 3(a), 8,9-anhydroerythromycin D 6,9-hemiacetal was converted to a reaction raw product, wherein de-(N-methyl)-(8S)-8-fluoroerythromycin D was identified by comparison with an authentic sample, as prepared by mono-demethylation of (8S)-8-fluoroerythromycin D, the latter having been obtained by fermentation carried out with *Streptomyces erythreus* ATCC 31772 using (8S)-8-fluoroerythronolide as the substrate (European Patent Application No. 82200019.6).

The N-mono-demethylation was carried out with $I_2$ in the presence of sodium acetate according to the method described in the example 3.

EXAMPLE 20

Preparation of (8S)-8-fluoroerythromycin D (Vd) by reductive methylation of de-(N-methyl)-(8S)-8-fluoroerythromycin D (IVd)

According to the general method of example 4, the crude product obtained in the example 19 was hydrogenated in the presence of 5% Pd/C and of 1% formaldehyde. The resulting solid residue was then purified by partition chromatography in a silica gel column as described in example 2, yielding (8S)-8-fluoroerythromycin D (Vd) having the same chemical and physical properties indicated in the example 17.

I claim:

1. A process for the preparation of (8S)-8-fluoroerthyromycins having the formula (V)

wherein R₁ is H or OH and R₂ is H or CH₃ comprising the following steps:

(a) reacting a compound having the formula wherein R₁ and R₂ have the above indicated meanings and x is 0 or 1, with an electrophilic fluorine-generating compound, giving the compound having the formula wherein R₁, R₂ and x have the above indicated meanings and R₃ is CH₃, when x=1, and R₃ is H, when x=0; and (b) reducing the compound given by step (a) and, when x=0, also methylating, yielding the corresponding compounds (V).

2. A process according to claim 1, wherein said electrophilic fluorine-generating compound is perchloryl fluoride, fluoroxy-perfluoroalkanes, fluoroxy-sulphur-pentafluoride, molecular fluorine, lead tetraacetate-hydrogen fluoride or trifluoroacetylhypofluorite.

3. A process according to claim 2, wherein said compound is fluoroxytrifluoromethane.

4. A process according to claim 2, wherein said compound is perchloryl fluoride.

5. A process according to claim 1, wherein step (a) is carried out in a reaction solvent selected from the group consisting of halogenated hydrocarbons, tetrahydrofuran, tetrahydrofuran diluted with water, dioxane, dioxane diluted with water, pyridine and mixtures thereof.

6. A process according to claim 5, wherein said reaction solvent is trichlorofluoromethane, chloroform, methylene chloride, or tetrahydrofuran and water.

7. A process according to claim 1, wherein the reaction temperature is between −75° C. and −85° C. or between −10° C. and +10° C.

8. A process according to claim 1, wherein said fluorination is carried out in the presence of a base.

9. A process according to claim 1, wherein said reduction is carried out by hydrogenation in the presence of a hydrogenation catalyst.

10. A process according to claim 9, wherein said catalyst is palladium supported on charcoal.

11. A process according to claim 9, wherein said reduction is carried out in a reaction solvent.

12. A process according to claim 10, wherein said reduction is carried out at room temperature.

13. A process according to claim 10, wherein said reduction is carried out at 1 atm. of hydrogen pressure.

14. A process according to claim 1, wherein said reduction is carried out in the presence of a methylating agent.

15. A process according to claim 14, wherein said methylating agent is formaldehyde.

16. A process according to claim 11, wherein said reaction solvent is selected from the group consisting of ethanol, methanol, tetrahydrofuran and ethyl acetate.

17. A process according to claim 8, wherein said base is calcium oxide, pyridine or potassium acetate.

18. A process according to claim 1, wherein said reduction is carried out in the presence of a hydrogenation catalyst comprising palladium supported on charcoal, in a reaction solvent selected from the group consisting of ethanol, methanol, tetrahydrofuran and ethyl acetate and in the presence of a methylating agent comprising formaldehyde.

19. (8S)-8-fluoroerythromycin N-oxides having the formula:

(II)

wherein R₁ is hydrogen or OH, and R₂ is hydrogen or methyl.

20. (8S)-8-fluoroerythromycin A N-oxide according to claim 19.

21. (8S)-8-fluoroerythromycin B N-oxide according to claim 19.

22. (8S)-8-fluoroerythromycin C N-oxide according to claim 19.

23. (8S)-8-fluoroerythromycin D N-oxide according to claim 19.

24. de-(N-methyl)-(8S)-8-fluoroerythromycins having the formula:
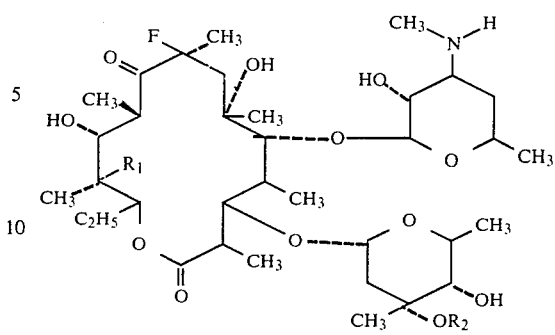
wherein $R_1$ is hydrogen or OH, and $R_2$ is hydrogen or methyl.
* * * * *